United States Patent [19]
Stolle et al.

[11] Patent Number: 5,849,349
[45] Date of Patent: Dec. 15, 1998

[54] ANTI-CHOLESTEROLEMIC EGG, VACCINE AND METHOD FOR PRODUCTION, AND USE

[75] Inventors: Ralph J. Stolle; Lee R. Beck, both of Lebanon, Ohio

[73] Assignee: DCV, Inc., Wilmington, Del.

[21] Appl. No.: 478,525

[22] Filed: Jun. 7, 1995

Related U.S. Application Data

[63] Continuation of Ser. No. 252,393, Jun. 1, 1994, abandoned, which is a continuation-in-part of Ser. No. 658,088, Feb. 20, 1991, abandoned, which is a continuation-in-part of Ser. No. 1,842, Jan. 9, 1987, abandoned, which is a continuation-in-part of Ser. No. 546,162, Oct. 27, 1983, Pat. No. 4,636,384, which is a continuation-in-part of Ser. No. 384,625, Jun. 3, 1982, abandoned, which is a continuation-in-part of Ser. No. 622,130, Jun. 19, 1984, Pat. No. 4,748,018, which is a continuation-in-part of Ser. No. 577,804, Feb. 7, 1984, abandoned.

[51] Int. Cl.$^6$ .............................. A01K 45/00; A23L 1/32; A61K 39/02; C12N 15/00
[52] U.S. Cl. ................. 426/614; 424/234.1; 424/184.1; 424/93.1; 424/87; 424/92; 119/6.8; 800/2
[58] Field of Search ................................. 800/2, DIG. 5, 800/6; 424/234.1, 784.1, 93.1, 87, 92; 426/614; 119/6.8

[56] References Cited

U.S. PATENT DOCUMENTS

| | | | |
|---|---|---|---|
| 3,128,230 | 4/1964 | Heinbach | 424/85 |
| 3,376,198 | 4/1968 | Petersen | 424/85 |
| 4,284,623 | 8/1981 | Beck | 424/85 |
| 4,324,782 | 4/1982 | Beck | 424/87 |
| 4,357,272 | 11/1982 | Polson | 424/85 |
| 4,410,541 | 10/1983 | Kamiral et al. | 424/273 R |
| 4,550,019 | 10/1985 | Polson | 424/85 |
| 4,636,384 | 1/1987 | Stolle et al. | 424/87 |
| 4,764,531 | 8/1988 | Nissen | 514/557 |
| 5,215,746 | 6/1993 | Stolle et al. | 424/92 |

FOREIGN PATENT DOCUMENTS

| | | |
|---|---|---|
| 1211876 | 11/1970 | United Kingdom . |
| 1442283 | 7/1976 | United Kingdom . |

OTHER PUBLICATIONS

Siegel et al, Poultry Science 63(9) pp. 1892–1894 (1984).
Ali, Dissertation Abstracts Int. B 1977 38(4) p. 1548.
Harrison, *Principles of Internal Medicine*, 10th Ed., pp. 1465–1475.
Lebacq–Verheyden et al., *Immunology*, 27:683–692 (1974).
Leslie et al., *J. Med.*, 130:1337–1352 (1969).
Polson et al., *Immunological Communications* 9:495–514 (1980).
Fertel et al., *Biochemical and Biophysical Research Communications* 102:1028–1033 (1981).
Jensenius et al., *Journal of Immunological Methods*, 46:63–68 (1981).
Polson et al., *Immunological Communications*, 9:475–493 (1980).
Davis et al., *Microbiology*, 3 ed., p. 294 (1980).
Duff et al., *J.Exper.Med.*, 89:611–630 (1949).
Martin et al., *Can.J.Biochem.Physiol.*, 36:153–160 (1958).
Burley et al., *Analytical Biochemistry*, 94:53–59 (1979).
Vesselinovitch et al., *Advances In Experimental Medicine and Biology*, 82:614–619.

*Primary Examiner*—Brian R. Stanton
*Attorney, Agent, or Firm*—Bell Seltzer Intellectual Property Law Group of Alston of Bird LLP

[57] ABSTRACT

Eggs that affect lipid and cholesterol levels obtained from avian species that are hyperimmunized against a variety of bacterial antigens are disclosed. These eggs are useful as a dietary supplement for humans and other animals.

11 Claims, No Drawings

ANTI-CHOLESTEROLEMIC EGG, VACCINE AND METHOD FOR PRODUCTION, AND USE

CROSS-REFERENCE TO RELATED DOCUMENTS

This application is a continuation of application Ser. No. 08/252,393, filed Jun. 1, 1994, (now abandoned); which is a continuation-in-part of application Ser. No. 07/658,088, filed Feb. 20, 1991, now abandoned; which is a continuation-in-part of application Ser. No. 07/001,842, filed Jan. 9, 1987, now abandoned; which is a continuation-in-part of application Ser. No. 06/546,162, filed Oct. 27, 1983 (now U.S. Pat. No. 4,636,384); which is a continuation-in-part of application Ser. No. 06/384,625, filed Jun. 3, 1982 (abandoned); which is a continuation-in-part of application Ser. No. 06/622,130, filed Jun. 19, 1984 (now U.S. Pat. No. 4,748,018); which is a continuation-in-part of application Ser. No. 06/577,804, filed Feb. 7, 1984 now abandoned.

BACKGROUND OF THE INVENTION

1. Field of the Invention

The present invention relates to avian eggs which do not increase the concentration of serum lipids in subjects consuming said eggs and to the use of said eggs for the treatment of disorders of the vascular systems, such as vascular aging and arteriosclerosis.

2. Description of the Background Art

The normal vascular system of mammals, especially humans, includes all of the organs, such as the heart and the arteries, involved in blood transport and circulation. Two major disorders affect the vascular system in animals: arteriosclerosis and aging. Arteriosclerosis, a generic term for the thickening and hardening of the arterial wall, is responsible for the majority of deaths in the United States and most westernized societies. There are various types of arteriolosclerosis, such as atherosclerosis, focal calcification, and arteriolosclerosis. The changes associated with arteriosclerosis (of the various types) and aging are partly overlapping. (See, for example, Harrison's "Principles of Internal Medicine," 10th edition, pp. 1465–1475.)

The normal artery wall consists of three reasonably well-defined layers: the intima, the media, and the adventitia. The intima is a layer of endothelial cells lining the lumen of all arteries. The endothelial cells are attached to each other by a series of junctional complexes and also are attached to an underlying meshwork of loose connecting tissue, the basal lamina. The lining of endothelial cells forms a barrier that controls the entry of substances from the blood into the arterial wall. The media consists of smooth muscle cells arranged in either single layers or multiple layers. The outermost layer of the artery is the adventitia which is delimited by the external elastic lamina. This external coat consists of a loose interwoven mixture of thick bundles of collagen, elastic fibers of varying size, and a mixture of smooth muscle cells and fibroblasts.

Maintenance of the endothelial cell lining is critical. Endothelial cell turnover occurs at a slow rate but may accelerate in focal areas by changing patterns of flow along the vessel wall. Intact endothelial cells function to prevent clotting, partly by elaboration of prostacyclin that inhibits platelet function, thereby enhancing unimpeded flow of blood. When the lining is damaged, however, platelets adhere to it, in part as the result of production of a different class of prostaglandins, the thromboxanes, and form a clot. The ability of the arterial wall to maintain the integrity of its endothelium, prevent platelet aggregation, and ensure the nutrition of its middle portion may be the critical determinants of the arteriosclerotic process.

The major change that occurs with normal aging in the arterial wall is a slow symmetrical increase in the thickness of the intima. This results from an accumulation of small muscle cells. In the nondiseased artery wall, the lipid content, mainly cholesterol ester and phospholipid, also progressively increases with age. While most of the phospholipid in the normal artery wall appears to be derived from in situ synthesis, the cholesterol ester that accumulates with aging appears to be derived from plasma, as it contains principally linoleic acid, the major plasma cholesterol ester fatty acid. As the normal artery ages, smooth muscle cells and connective tissue accumulate in the intima, leading to progressive thickening of the layer, coupled with progressive accumulation of fatty acid, resulting in a gradual increase in the rigidity of the vessels. The larger arteries may become dilated, elongated, and porous, and aneurysms may form in areas of encroaching degenerating arteriosclerotic plaque.

By far, the leading cause of death in the United States, both above and below age 65, is atherosclerosis, the atheromatous form of arteriosclerosis. The lesions are commonly classified as fatty streaks, fibrous plaques, and complicated lesions. The fatty streaks are characterized by an accumulation of lipid-filled smooth muscle cells and fibrous tissue in focal areas of the intima, and are stained distinctively by fat-soluble dyes. The lipid is mainly cholesterol oleate. Fibrous plaques are elevated areas of intima thickening, and will present the most characteristic lesion of advancing arteriosclerosis. They appear in the abdominal aorta, coronary arteries, and carotid arteries in the third decade, and increase progressively with age. Complicated lesions are calcified fibrous plaques containing various degrees of necrosis, thrombosis, and ulceration.

A number of "risk factors" have been identified in individuals who develop atherosclerosis. The risk factor concept implies that a person with at least one risk factor is more likely to develop a clinical atherosclerotic event and to do so earlier than a person with no risk factors. The presence of multiple risk factors further accelerates atherosclerosis. Among the reversible or partially reversible risk factors are hyperlipidemia (hypercholesterolemia and/or hypertriglyceridemia), hyperglycemia and diabetes mellitus, low levels of high-density lipoproteins in the presence of high concentrations of low-density lipoproteins, hypertension, obesity, and cigarette smoking.

As stated in Harrison's, supra (p. 1470), although the emergence of clinical consequences of atherosclerosis can be lessened, no convincing instance of regression or interruption of regression of atherosclerosis by removal or reversal of any single or group of risk factors has yet been proved in humans. The trend toward reduced smoking, lower cholesterol and fat consumption, reduction of bodyweight, and exercise programs have been helpful. Prevention, rather than grammar treatment, however, is the goal of public health professionals. An effective program of prophylaxis has not yet been established, although enough is known to guide in both identification of high risk and development of measures to reduce the risk.

Among the risk factors referred to above that might be particularly well-suited to therapeutic treatment is hyperlipidemia. Although control of factors such as obesity and cigarette consumption depend, to a great degree, on the will and inclination of individual, if a reasonable method for lowering total serum cholesterol, low-density lipoprotein cholesterol and triglycerides in the circulation were provided, it would be suitable for treatment of a broad spectrum of individuals.

Because of the widespread distribution of vascular disorders such as arteriosclerotic disorders and the naturally occurring aging of the vascular system and its accompanying problems, a need exists for an effective method both for preventing and possibly treating these disorders. If a natural food product, such as milk or eggs, for example, could be obtained having anti-arteriosclerotic and anti-aging effects, it would be an easily administratible, readily available, safe therapeutic composition.

It has been known in the prior art to produce milks having a variety of therapeutic effects. Beck, for example, has disclosed a milk containing antibody to *Streptococcus mutans* which has dental caries-inhibiting effects (Beck, U.S. Pat. No. 4,324,782). The milk is obtained by immunizing a cow with *S. mutans* antigen in two stages, and obtaining the therapeutic milk therefrom. Beck has also described a milk having anti-arthritic properties (copending U.S. Ser. No. 875,140, filed Feb. 6, 1978), and has described and patented a milk having anti-inflammatory properties (U.S. Pat. No. 4,284,623). Heinbach, U.S. Pat. No. 3,128,230, has described milk containing globulins of alpha, beta, and gamma components by inoculating a cow with antigenic mixtures. Petersen (U.S. Pat. No. 3,376,198 Canadian Patent 587,849), Holm (U.S. application (published) Ser. No. 628, 987), and Tunnak et al. (British Patent, 1,211,876) have also described antibody-containing milks. None of the aforementioned references, however, discloses or suggests milk having anti-arteriosclerotic, vascular anti-aging, or serum lipid-lowering properties.

It is well known to those skilled in the art of immunology that serum globulin fractions consisting of various antibody types such as IgA, IgM, and IgG can be used to counter the corresponding antigens, thereby neutralizing the effects of the antigens. The various antigens include carcinogenic, bacterial species, viral species, and bioregulatory factors of plant and animal origin, as well as toxins and poisons.

Normally, upon exposure to a foreign antigen, the immune system of an animal will neutralize the bioregulatory and/or harmful effects of the antigen. The exposure of the immune system of a given mammal to foreign antigens can occur either naturally, or the host may be exposed to the antigen by the intentional administration of antigen in the form of a vaccine. When an animal is vaccinated with an antigenic substance, an immune response results in which the subject produces antibodies. This process is generally referred to as active immunization of the host species exposed to antigen. The antibodies produced by any given species of animal by the process of active immunization are homologous antibodies to said given species of animal.

In a copending related patent application (U.S. Ser. No. 546,162, filed Oct. 27, 1983), there was disclosed a method for lowering blood lipid concentrations and thereby treating the aforementioned vascular disorders comprising feeding test animals and humans antibody-containing milk derived from cows maintained in a hyperimmune state by injections of polyvalent antigens derived from mixtures of bacteria.

It is known that various genera of the class Aves, such as chickens (*Gallus domesticus*), turkeys, and ducks, produce antibodies in their blood and in their eggs against factors which cause avian diseases, as well as against other antigens. For example, LeBacq-Verheyden et al., *Immunology* 27:683 (1974), and Leslie, G. A., et al., *J. Med.* 130:1337 (1969), have quantitatively analyzed immunoglobulins of the chicken. Polson, A., et al., *Immunological Communications* 9:495–514 (1980) immunized hens against several proteins and natural mixtures of proteins, and detected IgY antibodies in the yolks of the eggs. Fertel, R., et al., *Biochemical and Biophysical Research Communications* 102:1028–1033 (1981) immunized hens against prostaglandins and detected antibodies in the egg yolk. Jensenius et al., *Journal of Immunological Methods* 46:63–68 (1981), provide a method of isolating egg yolk IgG for use in immunodiagnostics. Polson et al., *Immunological Communications* 9:475–493 (1980), describe antibodies isolated from the yolk of hens that were immunized with a variety of plant viruses.

Poison, U.S. Pat. No. 4,357,272, discloses the isolation of antibodies from the yolks of eggs derived from hyperimmunized hens. The hyperimmunization was elicited by repetitive injections into the hens of antigens represented by plant viruses, human IgG, tetanus antitoxin, snake antivenines, and Serameba antigens. Polson, U.S. Pat. No. 4,550,019, discloses the isolation from egg yolks of antibodies raised in the hen by hyperimmunization with immunogens having a molecular or particle weight of at least 30,000. The antigens used to hyperimmunize the chickens were selected from among plant viruses, human immunoglobulins, tetanus toxin, and snake venoms.

The present invention is a further development over the invention disclosed and claimed in U.S. application Ser. No. 577,804, filed Feb. 4, 1984, by Beck and Stolle, for "Heterologous Protein Antibody Formulation for Passive Immunization," and in U.S. application Ser. No. 622,130, filed Jun. 19, 1984, by Stolle and Beck, for "Method of Passive Immunization of Mammals Using Avian Antibody." The entire disclosures of said applications are herein incorporated by reference.

In Ser. No. 577,804, there is disclosed a method of passive immunization of a mammal which comprises parenterally injecting a purified heterologous antibody obtained from the eggs of a domesticated fowl, which species has been immunized against an antigenic substance, and wherein the mammal has a history of consumption of eggs from such domesticated fowl. The invention disclosed in U.S. Ser. No. 622,130 expands on the concepts disclosed in U.S. Ser. No. 577,804, in that administration of the egg antibody can be by any appropriate route, not only parenteral.

All of these references, however, relate only to the isolation from hyperimmunized animals of immunoglobulins raised against various antigens and to the subsequent use of said immunoglobulins for either diagnostic procedures or homologous or heterologous passive immunization. No suggestion or speculation is made in these references either that the immunoglobulins produced against various antigens would have a beneficial effect on the lowering of serum lipid concentrations in animals or that said hyperimmunized eggs could be consumed by humans and other animals without elevating serum lipid concentrations.

SUMMARY OF THE INVENTION

It is an object of the invention to produce avian eggs which, when consumed by humans and other warm-blooded animals, will not increase the concentrations of serum lipids in said subjects.

It is also an object of the invention to provide avian eggs having beneficial effects upon disorders of the vascular systems.

The invention provides materials and a process for producing such avian eggs, said materials comprising bacterial antigens in vaccine form, and said process comprising immunization and hyperimmunization of avians with said bacterial antigen vaccine.

A further object of the invention is to provide a method for treating vascular disorders in humans and other warm-blooded animals.

These and other objects of the invention, which will hereinafter become more readily apparent, have been obtained by providing a method of treating vascular disorders in humans and other warm-blooded animals which comprises administering to said animal eggs collected from avian genera maintained in a hyperimmune state against specific bacterial antigens, in an amount sufficient to produce anti-arteriosclerotic, anti-aging vascular, or serum lipid-lowering effects. Further, by the present invention, avian eggs are provided which, upon consumption by humans and other warm blood animal, do not produce an elevation of serum cholesterol concentrations but rather, result in a lowering of serum cholesterol concentrations, said eggs being produced by avians being maintained in a hyperimmune state against specific bacterial antigens.

DETAILED DESCRIPTION OF THE PREFERRED EMBODIMENTS

As used hereinafter, the term "anti-cholesterolemic egg(s)" refers to the avian eggs of the present invention, said eggs produced by maintaining the animal producing said eggs in a hyperimmune state against a specific class of bacterial antigens, i.e. Gram negative bacteria common to the human digestive tract. The term "anti-cholesterolemic antigen(s)", as used hereinafter, shall mean antigens derived from those Gram-negative bacteria found in the human digestive tract. As used hereinafter this term "vaccine" refers to a suspension of bacteria or some antigenic part thereof which, when administered to an avian, results in the production of antibodies against said bacteria. Davis, B. D. et al., *Microbiology*, 3 ed., 1980, at 294.

The invention comprises a natural food product (anti-cholesterolemic eggs) which has beneficial properties toward animal vascular systems, as well as a method for producing and using same. The anti-cholesterolemic eggs of the present invention, being a natural product, can be used to treat vascular disorders associated with any disease or injury or a natural condition such as vascular aging in animals and humans, without fear of side effects.

Examples of vascular disorders which may be treated with the anti-cholesterolemic eggs of the present invention include aging disorders such as an increase in the rigidity of vessels and an increase in the incidence wherein the large arteries become dilated and elongated, as well as a decrease in aneurysms which form in areas of encroaching arteriosclerotic plaques. Other aging-induced vascular damage which can be prevented or reversed with the anti-cholesterolemic eggs of the present invention is the increase in the thickness of the arterial intima, the reversal of gradual accumulation of smooth muscle cells, as well as a decrease in the accumulation of lipid content in the arterial wall.

Among the abnormal (i.e., non-aging induced) disorders of the vascular system which are preventable or reversible with the anti-cholesterolemic eggs of the present invention is arteriosclerosis, which includes both atheromatous and non-atheromatous forms. Among the non-atheromatous forms of arteriosclerosis treatable with the eggs of the present invention is focal calcification (also called Monckberg's sclerosis), which is common in the lower extremities, upper extremities, and the arterial supply of the genital tract in both sexes. Another disorder is focal calcification, which involves degeneration of the smooth muscle cells followed by calcium deposition. Another non-atheromatous form of arteriosclerosis is arteriosclerosis which involves hyaline and general changes affecting both the intima and media of small arteries and arterials, particularly in the spleen, pancreas, adrenal, and kidney.

Importantly, the anti-cholesterolemic eggs of the present invention can be utilized for the treatment of atherosclerosis. This involves both the prevention and regression of the formation of fatty streaks, fibrous plaques, and complicated lesions, as described previously. Although it is probable that irreversible risk factors for atherosclerosis, such as male gender or genetic traits, might not be reversed with the eggs of the invention, the so-called reversible factor, however, may.

Thus, the anti-cholesterolemic eggs of the invention are useful in reducing the accumulation of lipids and preventing or reversing hypercholesterolemia or hypertriglyceridemia. Various forms of atherosclerosis can be treated.

Further, the anti-cholesterolemic eggs of the present invention are extremely valuable as a food source for egg protein. While avian eggs are known to be high in protein, conventional eggs, including the prior art eggs produced from immunized animals, have the undesirable characteristic of producing elevation in serum cholesterols upon consumption, even in normal healthy animals. The anti-cholesterolemic eggs of the present invention do not.

In the process of this invention, the source animal includes any egg-producing member of the class Aves, preferably, but not limited to, domesticated chickens (genus *Gallus domesticus*). Alternatively, genera represented by turkeys, ducks, geese, and the like may be used as the source of the hyperimmunized eggs.

The invention is based on the discovery that when such avians are brought to a specific state of immunization by means of periodic booster administrations of a specific class of bacterial antigen, or a mixture of such antigens, the animal will produce eggs which, when consumed, do not elevate serum cholesterol and other lipid concentrations and will have beneficial properties in the treatment of vascular disorders. These are "anti-cholesterolemic" eggs. The beneficial egg properties are not produced by all avians that are simply immunized. That is to say, the induction of immune sensitivity alone is insufficient to cause the appearance of the aforementioned anti-cholesterolemic properties in eggs, as is shown by the fact that normal fowl eggs do not contain these properties, even though fowl have become sensitized against various antigens during normal immunization against fowl diseases.

Furthermore, the properties are not always present in eggs produced by fowl maintained in the immune state by booster injection. It is only in a specific hyperimmune state that the eggs produced have the desired effect. This special state is achieved only by administering periodic boosters with sufficiently high doses of specific bacterial antigens or mixtures of such antigens. The preferred dose range should be equal to or greater than 50% of the dosage necessary to cause primary sensitization of the avian. Having knowledge of the requirement for developing and maintaining a hyperimmune state, it is within the skill of the art to vary the amount of bacterial antigen administered, depending upon the avian genera and strain employed, in order to maintain the animal in the hyperimmune state.

In summary, the process comprises the following steps:
1. Selection of bacterial antigen or antigens.
2. Sensitization of avians by primary immunization.
3. Administering boosters of bacterial antigens of appropriate dosage to induce and maintain a hyperimmune state.
4. Collecting eggs from the animal during the hyperimmune state.
5. Testing anti-aging or anti-arteriosclerotic properties of eggs collected from said hyperimmune avian.

Step 1-The method of treatment is to immunize the avian with a specific bacterial vaccine. The avian responds by producing antibodies in the eggs against the bacterial species used for the immunization. Specific egg antibodies produced in response to the immunization result in the anti-cholesterolemic factors. It was not known prior to the present teaching that avian antibodies produced against certain bacterial species and found in the eggs of said avians have anti-cholesterolemic properties. Table 1, which gives the bacterial species composition of 14 different vaccines used to immunize chickens, demonstrates that polyvalent vaccine A comprises 26 different bacterial species or subtypes. The results in Table 2 demonstrate that the eggs obtained from chickens immunized against polyvalent vaccine A contain the anti-cholesterolemic factor(s).

TABLE 1

Bacterial Species Composition of 14 Different Vaccines (A–N) Used to Immunize Chickens

| Bacteria | | Vaccine | | | | | | | | | | | | |
|---|---|---|---|---|---|---|---|---|---|---|---|---|---|---|
| | | A | B | C | D | E | F | G | H | I | J | K | L | N | N |
| Staph, aureus | | + | | + | | | | | | | | | | | |
| Staph, epidermidis | | + | | + | | | | | | | | | | | |
| Strep, pyogenes, A. | Type 1 | + | + | | | | | | | | | | | | |
| Strep. pyogenes, A. | 3 | + | + | | | | | | | | | | | | |
| Strep. pyogenes, A. | 5 | + | + | | | | | | | | | | | | |
| Strep. pyogenes, A. | 8 | + | + | | | | | | | | | | | | |
| Strep. pyogenes, A. | 12 | + | + | | | | | | | | | | | | |
| Strep. pyogenes, A. | 14 | + | + | | | | | | | | | | | | |
| Strep. pyogenes, A. | 18 | + | + | | | | | | | | | | | | |
| Strep. Pyogenes, A. | 22 | + | + | | | | | | | | | | | | |
| Aerobacter aerogenes | | + | | | | + | + | | | | | | | | |
| Escherichia coli | | + | | | | + | | + | | | | | | | |
| Salmonella enteritidis | | + | | | | + | | | + | | | | | | |
| Pseudomonas aeruginosa | | + | | | | + | | | | + | | | | | |
| Klebsiella pneumoniae | | + | | | | + | | | | | + | | | | |
| Salmonella pneumoniae | | + | | | | + | | | | | | + | | | |
| Haemophilis influenzae | | + | | | | + | | | | | | | + | | |
| Strep, mitis | | + | | | + | | | | | | | | | | |
| Proteus vulgaris | | + | | | | + | | | | | | | | + | |
| Shigella dysenteriae | | + | | | | + | | | | | | | | | + |
| Diplococcus pneumoniae | | + | | + | | | | | | | | | | | |
| Propionibacter acnes (anaerobe) | | + | | + | | | | | | | | | | | |
| Strep, sanguis | | + | | | + | | | | | | | | | | |
| Strep, salivarius | | + | | | + | | | | | | | | | | |
| Strep, mutans | | + | | | + | | | | | | | | | | |

TABLE 2

Autopsy Scores and Cholesterol Concentrations in Rabbits Fed Eggs Obtained from Chickens Hyperimmunized Against 14 Different Bacterial Vaccines

| Vaccine | No. of Rabbits & Rabbit Group | Autopsy Score[c] | | Cholesterol Levels | |
|---|---|---|---|---|---|
| | | Aorta | Liver | Serum (mg %) | Liver (mg/G) |
| Neg. Cont.[a] | 4; not given | 0 | 0 | 283 | 7.0 |
| Pos. Cont.[b] | 2; 38-8 | 5 | 5 | 764 | 9.3 |
| A | 4; 38-16 | 0 | 0 | 796 | 12.4 |
| B | 3; 38-12 | 5 | 5 | 560 | 12.9 |
| C | 1; 38-13 | 5 | 5 | 1600 | 22.5 |
| D | 2; 38-14 | 5 | 5 | 1210 | 28.5 |
| E | 1; 38-15 | 0 | 0 | 428 | 8.9 |
| F | 3; 38-19 | −2 | 0 | 271 | 7.9 |
| G | 3; 38-20 | 1 | 0 | 388 | 11.9 |
| H | 2; 38-21 | 2 | 3 | 495 | 13.9 |
| I | 2; 38-22 | 4 | 3 | 551 | 13.3 |

TABLE 2-continued

Autopsy Scores and Cholesterol Concentrations
in Rabbits Fed Eggs Obtained from Chickens
Hyperimmunized Against 14 Different Bacterial Vaccines

| Vaccine | No. of Rabbits & Rabbit Group | Autopsy Score[c] | | Cholesterol Levels | |
|---|---|---|---|---|---|
| | | Aorta | Liver | Serum (mg %) | Liver (mg/G) |
| J | 3; 38-23 | 4 | 3 | 574 | 12.3 |
| K | 2; 38-24 | 5 | 5 | 472 | 25.9 |
| L | 2; 38-25 | 5 | 5 | 683 | 27.9 |
| M | 3; 38-26 | 5 | 5 | 706 | 23.6 |
| N | 3; 38-27 | 2 | 5 | 868 | 35.8 |

[a]Rabbits not fed eggs.
[b]Rabbits fed eggs from non-hyperimmunized chickens.
[c]0 is equivalent to negative control; 5 is equivalent to positive control.

The next step was to determine which specific bacterial species or combination of species contained in polyvalent vaccine A produced the anti-cholesterolemic antibody. This was done systematically by the process of elimination. Polyvalent vaccine A was first divided into four subgroups, B through E. The identification of the bacterial species in each of the subgroups is shown in Table 1. As summarized in the data in Table 2, the anti-cholesterolemic effect was absent in test animals (rabbits) fed eggs derived from fowl given from vaccine groups B, C, and D. The anti-cholesterolemic effect was present in the chickens immunized against bacterial vaccine group E.

When the component bacteria in vaccine group E were individually evaluated, the results, which are summarized in Table 2, demonstrate that there was no anti-cholesterolemic effects in rabbits fed eggs from chickens immunized against four of the individual bacterial species included in vaccine E (vaccines K, L, M, and N). There was, however, an anti-cholesterolemic effect observed in test animals fed eggs from chickens immunized against five of the bacterial species of vaccine E (vaccines F, G, H, I, and J). The anti-cholesterolemic effect varied from complete protection to slight protection, as indicated by the different scores ranging between 0 and 5. The eggs obtained from chickens immunized against *Aerobacter aerogenes* gave the greatest level of protection, followed next by *Escherichia coli*. Moderate protection was provided by *Salmonella enteritidis* and *Pseudomonas aeruginosa*. *Shigella dysenteriae* gave only slight protection. The bacterial species that produce anti-cholesterolemic antibodies in the chicken have three things in common. They are all Gram-negative staining bacteria, all reside in the lower intestinal tract of man, and all are pathogenic. Thus the anti-cholerolemic antigens of the present invention comprise that class of bacterial antigens which are (1) Gram-negative, (2) found in the human gut, and (3) pathogenic.

Step 2-Antigens can be administered by any method which causes sensitization. The preferred method of immunization is by intramuscular injection. The preferred method of administration of the antigens to chickens is in the breast muscle. The dosage is preferably 1–5 mg of the mixed bacterial vaccine. Repeated immunizations are given at intervals, preferably two-week, over a suitable period of time, preferably six months.

It can be determined whether or not the avian has become sensitive to the antigen. There are a number of methods known to those of skill in the art of immunology to test for sensitivity. *Methods in Immunology and Immunochemistry*, Williams, C. A., Chase, W. N., Academic Press, N.Y., London (Vols. 1–5) (1977). The appearance of egg antibodies after immunization with the vaccine is indicative of sensitivity. The minimum dose of antigen necessary to induce hypersensitivity depends on the type of antigen used.

Step 3 involves the induction and maintenance of the hyperimmune state. This state is induced by repeated booster administration of an appropriate dosage at fixed-time intervals, preferably two-week intervals over a six-month period of time where polyvalent bacterial agents are employed. Moreover, the booster administration must not induce a state of immune tolerance. This will cause the animal to pass from a hyperimmune state to a state of immune tolerance to the antigen, in which case the animal will cease to produce eggs with the beneficial properties.

It might also be possible, for example, to use a combination of different immunization procedures, i.e., intramuscular injection for primary immunization and intravenous injection for booster injections, etc. Many different combinations of immunization might be employed by those skilled in the arts to: (1) sensitize and (2) induce the hyperimmune state.

Step 4 involves collection and processing of the eggs. If the eggs are to be processed into dried egg powders, freeze-drying (lyophilization) is the preferred method. Whole eggs can also be used, as well as eggs that have been separated into egg yolks and egg white. It should be remembered that the beneficial antibodies are present in the egg yolk.

Step 5 is to test the serum lipid lowering and vascular disorder treatment properties of the eggs. A battery of research techniques can be used to test the effects of the hyperimmune eggs on the vascular system of animals. Preferably, suitable strains of rabbits are used as the test animal. Such animals, being susceptible to hypercholesterolemia, hyperlipidemia and atherosclerosis, are a well-established animal model for these disease entities in man. Duff, G. L., et al., *J. Exper. Med.* 89:611–630 (1949), at 612. These tests include in all cases feeding said test rabbit a diet which comprises hyperimmune eggs (with a control comprising animals with a diet containing normal eggs and another control comprising animals with an egg-free diet). After a predetermined period of time, preferably feeding rabbits one egg a day for 90 days with the egg being mixed with the drinking water of the rabbit, the rabbits are sacrificed and autopsies performed. The livers and aortas of the rabbits are dissected and examined for fatty deposits. Samples of these tissues are examined by standard histological methods to evaluate the level of lipid deposits in both the liver and aorta. A scoring system can be used to compare the degree of lipid deposits observed in the livers and aortas among the treatment and control groups. The following scoring system was preferred. The liver and aortas of each rabbit are dissected and given a score of 0–5, depending upon the amount of lipid deposits that were observed. A score of 0 is equivalent to a control that was not fed eggs, and a score of 5 is equivalent to controls fed normal chicken eggs. Histological sections are evaluated by the same criteria. The average score of each group of animals is then calculated. According to this scoring system, a mean score of 0 would indicate complete prevention of lipid deposits in the liver and aorta due to egg cholesterol in the diet, whereas a score of 5 would indicate no protection. Scores between 0 and 5 would indicate intermediate levels of protection, 1 being greater than 2, etc. In addition to this, the quantity of lipid in the blood and in liver and heart tissues can be measured using standard biochemical methods.

The results shown in Table 2 demonstrate that the eggs obtained from chickens beginning one month after the first immunization against the mixed bacterial vaccine (vaccine A) contain the anti-cholesterolemic factor. Having once developed a suitable protocol for immunization and hyperimmunization, anti-cholesterolemic eggs may be readily produced on a commercial scale, with only a minimum of spot-checking required.

The histological examination of blood vessels and liver can include any of the following techniques: scanning electron microscopy of the endocardial surfaces of the heart searching for endothelial damage; transmission electron microscopy of vessels searching for lipid droplets, endothelial degeneration, lipid presence in thome cells, or a tendency of fibrin or platelets to adhere to the lumenal surface of endothelial cells; histological analyses of hearts searching for lipid, e.g., cholesterol; demonstration of lipids with oil-soluble dyes such as oil red or Sudan black in sections of frozen tissues, or the presence of enzymes, especially cytochrome oxidase.

The present invention is based in part on the discovery that anti-cholesterolemic eggs have beneficial properties on the cardiovascular system. For example, it has been discovered that in hearts of female rabbits which have been fed a steady diet of anti-cholesterolemic eggs, the endothelial cells of the heart are protected against extensive endothelial damage of varying extent and severity observed in rabbits fed normal eggs with their well known high cholesterol content. In the latter rabbits, craters or holes are present where one or more cells have degenerated and detached, whereas in anti-cholesterolemic hyperimmune egg-fed rabbits, these were not present. Transmission electron microscopy of both populations of rabbits show major differences in the blood vessels. Significant pathological features of blood vessels in control hearts include large lipid droplets, endothelial degeneration, multiple small lipid vacuoles, single or multiple large lipid droplets filling the cytoplasm of endothelial cells, foam cells latent with lipid, and a strong tendency of fibrin platelets to adhere to the lumenal surface of endothelial cells. All of the aforementioned derangement accompany the pathogenesis of atherosclerosis. These derangements are not found in blood vessels from representative areas of rabbit populations that are on a steady diet of hyperimmune eggs. Histological sections of hearts from the rabbits fed the hyperimmune eggs or milk and of rabbits fed control eggs or milk show that lipid is present in the lumena of some blood vessels of control hearts, and cardiac muscle fibers of control hearts are filled with lipid. Coronary blood vessels from rabbits on hyperimmune eggs lack the atherosclerotic lipid deposits which are observed in control vessels. These results demonstrate that anti-cholesterolemic eggs slow and/or repress the pathogenesis of arteriosclerosis and aging of the heart. The same tests on rabbit populations demonstrate that diets incorporating the hyperimmune eggs of this invention, not only result in a reduction of the concentrations of serum cholesterol, triglycerides, and low-density lipoproteins, all of which are key factors associated with cardiovascular disease, but also fail to bring about the increase in said serum lipids generally observed in humans (and other warm-blooded animals) who consume eggs.

The eggs of the invention can be provided in any amount which effects or maintains the reversal of vascular disorders in warm-blooded animals.

The same amounts can be utilized in normal subjects when operating in a preventive mode. The whole eggs or egg yolks can be incorporated into any food product, as long as the food product is not treated at a temperature which is too elevated and which would thereby inactivate the beneficial properties of the product.

Further, it has been found that the yolk fractions contain the agent or agents responsible for the beneficial properties observed and referred to above. Those of ordinary skill in the art, knowing that the yolk fraction contains the factors of importance, would clearly recognize that further separation can be made to obtain more potent fractions.

Having now generally described this invention, the same will be further described by reference to certain specific examples which are provided herein for purposes of illustration only and are not intended to be limiting unless otherwise specified.

EXAMPLE 1

Five chickens were immunized against polyvalent bacterial vaccine A (cf., Table 1).

Bacterial cultures were obtained from the American Type Culture Collection (ATCC). They were reconstituted with media, and incubated overnight at 37° C. About half of each bacterial suspension was used to inoculate one liter of broth, which was cultured at 37° C. The remaining suspension was stored in sterile glycerol at −20° C. After good growth was apparent, bacteria were harvested by centrifugation of 14,000×g for 20 mins. The pellet of bacteria was washed by repeated (3×) suspension in saline and reisolation by centrifugation. Washed pellets were suspended in a small volume of distilled water, and bacteria were heat-killed by maintenance at 80° C. overnight. Heat-killed bacteria were lyophilized and stored in sterile vials at −20° C.

An amount of bacterial antigen sufficient to immunize up to 10 adult female chickens was prepared as follows. About 350 mg of mixed bacterial powder was suspended in 1 liter of sterile saline to a concentration of approximately $202 \times 10^8$ bacterial cells/ml. saline ($A_{660}=1.0$). One milliliter of this mixture was injected into each chicken.

Repeated immunizations were given at two-week intervals over a six-month period of time.

Eggs were collected from chickens beginning one month after the first immunization. Rabbits, which are known to be a valid model of human arteriosclerosis (Duff et al. supra), were fed one egg a day for 90 consecutive days. The eggs were mixed with the drinking water of the rabbit. Three rabbits were fed the eggs obtained from the chickens immunized against polyvalent vaccine A. Six additional rabbits were used as controls. One control group of three rabbits were fed eggs from non-immunized chickens, and the other control group of three rabbits was fed the same daily ration of rabbit food, but no eggs. After 90 days, the rabbits were sacrificed and autopsies were performed. The livers and aortas of the rabbits were dissected and examined for fatty deposits. Samples of these tissues were examined by standard histological methods to evaluate the level of lipid deposits in both the liver and aorta. Serum and liver lipid concentrations were estimated by standard chemical analysis.

The results shown in Table 2 show that the eggs obtained from chickens immunized against the polyvalent bacterial vaccine A contain the anti-cholesterolemic factor.

EXAMPLE 2

Five chickens were immunized with each of vaccine groups B through E listed in Table 1, according to the protocol described in Example 1 above. Eggs obtained from these chickens were evaluated in rabbits according to the same procedure described above in Example 1. Results from these rabbit experiments are summarized in Table 2. The anti-cholesterolemic effect is absent in rabbits fed eggs of vaccine groups B, C, and D, but the anti-cholesterolemic effect was present in rabbits immunized against bacterial vaccine group E.

EXAMPLE 3

Groups of five chickens each were immunized with each of the nine individual bacterial species included in vaccine E of Table 1, according to the protocol of Example 1. Eggs from these chickens were fed to rabbits according to the same experimental protocol described above in Example 1. The results from this series of experiments, which are summarized in Table 2, demonstrate that there was no anti-cholesterolemic effects in rabbits fed eggs from chickens immunized against four of the individual bacterial species included in vaccine group E. There was, however, an anti-cholesterolemic effect observed in rabbits fed eggs from chickens immunized against five of these bacterial species, namely, *Aerobacter aerogenes, Escherichia coli, Salmonella enteridites, Pseudomonas aeruginosa,* and *Shigella dysenteriae*. These five bacteria are all Gram-negative staining bacteria, all reside in the lower intestinal tract of humans, and all are pathogenic in man.

What is new and intended to be covered by Letters Patent of the United States is:

1. An avian egg containing at least one factor, wherein said factor, when present in said egg, produces, upon ingestion of said egg, a level of lipid deposits in the aorta of a mammal ingesting said egg that is lower than the level of lipid deposits found in the aorta of said mammal prior to ingesting said egg, and wherein the cholesterol level in said egg is within the normal physiological range of cholesterol levels, said factor being produced in the egg of an avian that has been hyperimmunized, during egg production, with at least one antigen from *Aerobacter aerogenes*.

2. An avian egg containing at least one factor, wherein said factor, when present in said egg, produces, upon ingestion of said egg, a level of lipid deposits in the aorta of a mammal ingesting said egg that is lower than the level of lipid deposits found in the aorta of said mammal prior to ingesting said egg, and wherein the cholesterol level in said egg is within the normal physiological range of cholesterol levels, said avian egg being produced by a process comprising:

sensitizing a female avian with a mixture of one or more antigens, wherein said antigens are prepared from *Aerobacter aerogenes;* administering boosters of said one or more antigens at a dosage sufficient to induce and maintain and hyperimmune state in said female avian; and collecting said avian egg from said female avian.

3. An avian egg containing at least one factor, wherein said factor when present in said egg, produces, upon ingestion of said egg, serum cholesterol levels in a mammal ingesting said egg that are lower than the serum cholesterol levels found in said mammal ingesting a normal egg, and wherein the cholesterol level in said egg is within the normal physiological range of cholesterol levels in avian eggs, said factor being produced in the egg of an avian that has been hyperimmunized, during egg production, with at least one antigen from at least one bacterial strain, said strain being selected from the group consisting of *Aerobacter aerogenes, Escherichia coli, Salmonella enteriditis, Pseudomonas aeruginosa, Klebsiella pneumoniae, Salmonella typhimurium, Haemophilus influenzae, Proteus vulgaris* and *Streptococcus pyogenes,* A.

4. An avian egg containing at least one factor, wherein said factor, when present in said egg, produces, upon ingestion of said egg, serum cholesterol levels in a mammal ingesting said egg that are lower than the serum cholesterol levels found in said mammal ingesting a normal egg, and wherein the cholesterol level in said egg is within the normal physiological range of cholesterol levels, said avian egg being produced by a process comprising:

sensitizing a female avian with a mixture of one or more antigens, wherein said antigens are prepared from each of the following strains: *Aerobacter aerogenes, Escherichia coli, Salmonella enteritidis, Pseudomonas aeruginosa, Klebsiella pneumoniae, Salmonella typhimurium, Haemophilus influenzae, Proteus vulgaris,* and *Shigella dysenteriae;* administering boosters of said one or more antigens at a dosage sufficient to induce and maintain and hyperimmune state in said female avian; and collecting said avian egg from said female avian.

5. An avian egg containing at least one factor, wherein said factor, when present in said egg, maintains the level of lipid deposits in the liver of a mammal ingesting said egg, and wherein the cholesterol level in said egg is within the normal physiological range of cholesterol levels in avian eggs, said factor being produced in the egg of an avian that has been hyperimmunized during egg production, with at least one antigen from at least one bacterial strain, said bacterial strain selected from the group consisting of *Aerobacter aerogenes* and *Escherichia coli.*

6. An avian egg containing at least one factor, wherein said factor, when present in said egg, maintains, the level of lipid deposits in the liver of a mammal ingesting said egg, and wherein the cholesterol level in said egg is within the normal physiological range of cholesterol levels, said avian egg being produced by a process comprising:

sensitizing a female avian with a mixture of one or more antigens, wherein said antigens are prepared from a bacterial strain selected from the group consisting of *Aerobacter aerogenes* and *Escherichia coli;* administering boosters of said one or more antigens at a dosage sufficient to induce and maintain and hyperimmune state in said female avian; and collecting said avian egg from said female avian.

7. An avian egg containing at least one factor, wherein said factor, when present in said egg, produces serum cholesterol levels in a mammal ingesting said egg that are lower than the serum cholesterol levels found in said mammal ingesting a normal egg, and wherein the cholesterol level in said egg is within the normal physiological range of cholesterol levels, said avian egg being produced by a process comprising:

sensitizing a female avian with a mixture of one or more antigens, wherein said antigens are prepared from a bacterial strain selected from the group consisting of *Streptococcus pyrogenes* A., *Aerobacter aerogenes, Escherichia coli, Salmonella enteritidis, Pseudomonas aeruginosa, Klebsiella pneumoniae, Salmonella typhimurium, Haemophilus influenzae,* and *Proteus vulgaris,* administering boosters of said one or more antigens at a dosage sufficient to induce and maintain and hyperimmune state in said female avian; and collecting said avian egg from said female avian.

8. An avian egg containing at least one factor, wherein said factor, when present in said egg, produces, upon ingestion of said egg, a level of lipid deposits in the aorta of a mammal ingesting said egg that are lower than the level of lipid deposits found in the aorta of a mammal ingesting a normal egg, and wherein the cholesterol level in said egg is within the normal physiological range of cholesterol levels, said factor being produced in the egg of an avian that has been hyperimmunized, during egg production, with at least one antigen from at least one bacterial strain, said strain being selected from the group consisting of: *Escherichia coli, Salmonella enteritidis, Pseudomonas aeruginosa, Klebsiella pneumoniae,* and *Shigella dysenteriae.*

9. An avian egg containing at least one factor, wherein said factor, when present in said egg, does not increase the level of lipid deposits in the aorta of a mammal ingesting said egg to the level of lipid deposits in the aorta of a mammal ingesting a normal egg, and wherein the cholesterol level in said egg is within the normal physiological range of cholesterol levels, said avian egg being produced by a process comprising:

sensitizing a female avian with a mixture of one or more antigens, wherein said antigens are prepared from a bacterial strain selected from the group consisting of *Escherichia coli, Salmonella enteritidis, Pseudomonas aeruginosa, Klebsiella pneumoniae,* and *Shigella dysenteriae;* administering boosters of said one or more antigens at a dosage sufficient to induce and maintain and hyperimmune state in said female avian; and collecting said avian egg from said female avian.

10. An avian egg containing at least one factor, wherein said factor, when present in said egg, produces, upon ingestion of said egg, a level of lipid deposits in the liver of a mammal that is lower than the level of lipid deposits found in the liver of a mammal ingesting a normal egg, and wherein the cholesterol level in said egg is within the normal physiological range of cholesterol levels, said factor being produced in the egg of an avian that has been hyperimmunized, during egg production, with at least one antigen from at least one bacterial strain, said strain being selected from the group consisting of *Salmonella enteritidis, Pseudomonas aeruginosa,* and *Klebsiella pneumoniae.*

11. An avian egg containing at least one factor, wherein said factor, when present in said egg, a level of lipid deposits in the liver of a mammal ingesting said egg that is lower than the level of lipid deposits in the liver of mammal ingesting a normal egg, and wherein the cholesterol level in said egg is within the normal physiological range of cholesterol levels, said avian egg being produced by a process comprising:

sensitizing a female avian with a mixture of one or more antigens, wherein said antigens are prepared from a bacterial strain selected from the group consisting of *Salmonella eneritidis, Pseudomonas aeruginosa,* and *Klebsiella pneumoniae;* administering boosters of said one or more antigens at a dosage sufficient to induce and maintain and hyperimmune state in said female avian; and collecting said avian egg from said female avian.

* * * * *